US005716921A

United States Patent [19]

Neumiller

[11] Patent Number: 5,716,921

[45] Date of Patent: Feb. 10, 1998

[54] GLASS CLEANER WITH ENHANCED ANTIFOG PROPERTIES

[76] Inventor: Phillip J. Neumiller, 4734 W. Knollwood Dr., Racine, Wis. 53403

[21] Appl. No.: 630,233

[22] Filed: Apr. 10, 1996

Related U.S. Application Data

[63] Continuation of Ser. No. 255,635, Jun. 9, 1994, abandoned.

[51] Int. Cl.[6] ........ A61K 7/047

[52] U.S. Cl. ........ 510/181; 510/182; 510/237; 510/423; 510/477; 510/501; 510/504; 510/506; 106/13

[58] Field of Search ........ 510/181, 182, 510/237, 384, 421, 422, 423, 477, 405, 501, 504, 506; 106/13

[56] References Cited

U.S. PATENT DOCUMENTS

| | | | |
|---|---|---|---|
| 3,696,043 | 10/1972 | Labarge | 252/153 |
| 3,819,522 | 6/1974 | Zmoda et al. . | |
| 3,939,090 | 2/1976 | Zmoda . | |
| 4,284,435 | 8/1981 | Fox | 134/2 |
| 4,315,828 | 2/1982 | Church . | |
| 4,414,128 | 11/1983 | Goffinet | 252/111 |
| 4,565,609 | 1/1986 | Nobel et al. | 204/44.4 |
| 4,701,244 | 10/1987 | Nobel et al. | 204/44.4 |
| 4,769,169 | 9/1988 | Fishlock-Lomax | 252/106 |
| 4,921,629 | 5/1990 | Malihi et al. | 252/170 |
| 5,057,303 | 10/1991 | Casey | 424/7.1 |
| 5,064,635 | 11/1991 | Casey | 424/7.1 |
| 5,108,660 | 4/1992 | Michael | 252/545 |
| 5,110,492 | 5/1992 | Casey | 252/90 |
| 5,252,245 | 10/1993 | Garabedian, Jr. et al. | 252/153 |
| 5,254,284 | 10/1993 | Barone et al. . | |
| 5,296,338 | 3/1994 | Chester | 430/372 |
| 5,362,422 | 11/1994 | Masters | 252/544 |
| 5,536,451 | 7/1996 | Masters et al. | 510/405 |

FOREIGN PATENT DOCUMENTS

595383A1 5/1994 European Pat. Off. .

OTHER PUBLICATIONS

Witco Data Sheets 1/92 & 3/92 for Rewoteric AMV and Rewoteric AM 2CSF.

*Primary Examiner*—Paul Lieberman
*Assistant Examiner*—John R. Hardee
*Attorney, Agent, or Firm*—Laura L. Bozek

[57] ABSTRACT

Aqueous glass cleaning compositions with optimal antifog properties contain a quaternary compound and an amphoteric surfactant having the formula

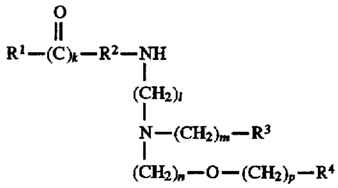

wherein:

$R^1$ and $R^2$ are independently alkyl groups or $R^2$ is a single bond (wherein $R^1+R^2$ is $C_{6-14}$), k is 0 or 1, l is 1–6, m is 1–4, $R^3$ is —$CH_2OH$ or —COOM (wherein M is H or alkali metal), n is 1–4, p is 1–4 and $R^4$ is —COOM.

20 Claims, No Drawings

GLASS CLEANER WITH ENHANCED ANTIFOG PROPERTIES

This application is a continuation of application Ser. No. 08/255,635 filed on Jun. 9, 1994, now abandoned.

BACKGROUND OF THE INVENTION

1. Field of the Invention

The present invention relates generally to compositions for cleaning glass surfaces. In particular, the present invention relates to improved antifog glass cleaning compositions.

2. Brief Description of the Background Art

It is commonly understood that good glass cleaners desirably provide within a single composition various disparate characteristics. These characteristics optimally include good detergency, acceptable evaporability, streak-resistance and the like. In view of the often contradictory nature of these features, it has proven quite difficult to produce a glass cleaner which attains them all.

Typical prior art liquid glass cleaners utilize a water-based system with detergent and an organic solvent. For reasons of household safety and commercial acceptance, glass cleaners are nearly universally water based. However, water soluble organic detergents generally exhibit poor detergency. While detergent builders increase detergency by sequestering polyvalent metal ions, inorganic builders are recognized in the art to cause filming and streaking.

Generally, the glass cleaner is applied to a contaminated surface to loosen dirt while emulsifying oil and grease. The offending solubilized materials are thereafter wiped from the contaminated surface. If the oil and grease are not completely emulsified, or are not completely transferred to the wiping material, streaking and smearing occurs. U.S. Pat. No. 4,315,828 relates to aqueous glass cleaning compositions containing polyethylene glycol or methoxypolyethylene glycol to provide a coating on the glass to repel the emulsified oil and grease, thereby enhancing its transfer to the toweling and provide a streakless cleaner.

Other problems arise when relatively cool non-porous surfaces are exposed to a warm moist atmosphere, since the cool surface will become fogged. In particular, glass fogging occurs by the condensation of steam or water vapor when the surface temperature of the non-porous surface is below the dewpoint. The opaque fog is therefore caused by the condensation of moisture droplets onto the non-porous surface. Naturally, this is undesirable for windows, mirrors, face masks, spectacles and the like.

The prior art recognizes that fogging may be averted by a variety of means, including providing double-pane sheets to isolate the cooler glass pane from the warmer moist atmosphere. However, this is not practicable for many devices, such as mirrors. It is also possible to treat the surface to increase its porosity. However, increasing the porosity of surfaces obviously degrades the optical characteristics of mirrors, windows and the like. Other methods of avoiding fogging include treating the non-porous surface with hydrophilic chemicals that tend to decrease the incidence of droplet formation. In general, such surface active agents reduce the surface tension of the glass and encourage the individual water droplets to coalesce into a sheet. However, these materials may also impart undesirable optical properties to the treated surface. Such methods include those taught by U.S. Pat. No. 5,254,284, which relates to a cleaning composition containing silicone glycol and relates the prior use of hexamethylcyclotrisiloxane and silicofluorocarbon compounds for that purpose.

U.S. Pat. No. 5,108,660 relates to aqueous glass cleaning compositions containing a hydrocarbylamidoalkylene sulfobetaine detergent surfactant in order to reduce the level of filming and streaking. These compositions are also said to solubilize greater amounts of hydrophobic perfumes than the prior art and exhibit a reduced tendency to fog up, particularly when combined with an additional organic anionic or nonionic surfactant, typically a $C_{12-18}$ acylamido alkylene amino alkylene sulfonate.

Nonetheless, other materials inhibit fogging by atmospheric moisture for reasons that are less apparent. For instance, U.S. Pat. No. 5,254,284 also shows that the anti-fogging properties of silicone glycol are improved by the co-addition of xanthan gum, even though xanthan gum is not, by itself, an anti-fogging agent.

U.S. Pat. No. 3,939,090 relates to compositions for cleaning glass comprising a copolymer having monomer units of (i) an ethylenically unsaturated carboxylic acid anhydride or partial ester and (ii) an ethylenically unsaturated non-carboxylic containing monomer. The copolymer is said to be a mild film former which hardens the window cleaner residue remaining on the glass after use.

U.S. Pat. No. 3,819,522 relates to non-fogging glass cleaning compositions containing an acetylenic glycol. The acetylenic glycol exhibits no significant antifogging properties by itself, but is provided with antifogging capability by admixture with an anionic or nonionic surfactant.

SUMMARY OF THE INVENTION

It is an object of the present invention to provide a novel antifog glass cleaning composition.

It is also an object of the present invention to provide a glass cleaning composition with superior wetting and sheeting properties.

It is a further object of the present invention to provide a glass cleaning composition which precludes the formation of water spots.

An additional object of the present invention is to provide a glass cleaning composition with good streak resistance.

These objects and others are provided by a novel aqueous composition which comprises a quaternary compound and an amphoteric surfactant having a lipophilic portion, a cationic portion and an anionic portion containing an ether linkage.

In particular, the compositions according to the present invention exhibit excellent antifog properties. The compositions of the present invention compare quite favorably to window cleaning liquids presently available commercially, such as those sold under the tradenames Rain-X® Anti-Fog, Amway SEE Spray® Steam-Barrier Formula and the like. Amway SEE Spray® Steam-Barrier Formula provides acceptable antifog activity, using an ethoxylated silicone, ammonia and an anionic surfactant. Rain-X® Anti-Fog is believed to utilize fatty acid soaps to provide fair antifog activity, but results in treated glass surfaces with streaking and blooming.

DETAILED DESCRIPTION OF THE INVENTION

The above features and advantages are provided by the present invention which relates most generally to an aqueous glass cleaning composition comprising a combination of at least one amphoteric compound and at least one quaternary compound. If desired, these compositions may also contain one or more of the following: an organic solvent, coloring and fragrance. The composition may also contain other conventional materials including, but certainly not limited to, ammonia, vinegar, chelating agents, pH modifiers, hydrotropes, antimicrobial compounds, etc.

The amphoteric compound utilized in the present invention is a surfactant. Generally, nonionic and cationic amphoteric surfactants result to various extents in glass cleaners with streaking problems. Accordingly, the amphoteric surfactants preferred for use in the present invention are employed under alkaline conditions to render active the anionic portion of the amphoteric compound.

In this regard, the present inventor has determined that the antifog activity of the amphoteric compound is facilitated by the anionic portion or moiety of the amphoteric surfactant. The lipophilic portion is believed to be less critical to antifog function and the cationic portion of the amphoteric compound is believed not to be particularly responsible for antifog activity.

Desirably, the amphoteric surfactants which are employed in this invention have the formula

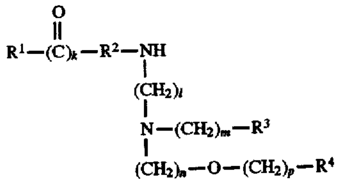

wherein:

$R^1$ and $R^2$ are independently alkyl groups or $R^2$ is a single bond (wherein $R^1$+$R^2$ is $C_{6-14}$), k is 0 or 1, l is 1–6, m is 1–4, $R^3$ is —$CH_2OH$ or —COOM (wherein M is H or alkali metal), n is 1–4, p is 1–4 and $R^4$ is —COOM.

Preferably, $R^1$ and $R^2$ are independently alkyl groups or $R^2$ is a single bond (wherein $R^1$+$R^2$ is $C_{8-12}$), k is 0 or 1, l is 1–4, m is 1–3, $R^3$ is —$CH_2OH$ or —COOM (wherein M is H or alkali metal), n is 1–3, p is 1–3 and $R^4$ is —COOM.

More preferably, $R^1$ is $C_{8-12}$ alkyl, $R^2$ is a single bond, k is 1, l is 1–3, m is 1 or 2, $R^3$ is —COOM (wherein M is H or alkali metal), n is 1 or 2, p is 1 or 2 and $R^4$ is —COOM.

Most preferably, $R^1$ is $C_9$ alkyl, $R^2$ is single bond, k is 1, l is 2, m is 2, $R^3$ is —COOM (wherein M is H or alkali metal), n is 2, p is 1 and $R^4$ is —COOM.

Preferably, the amphoteric surfactant exhibits a high detergency and has a low foam characteristic. Suitable examples of such amphoteric compounds include the following formulae (I) and (II):

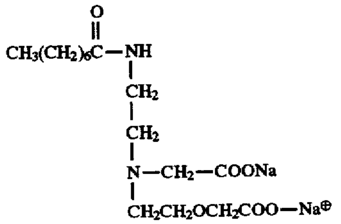

(I)

-continued

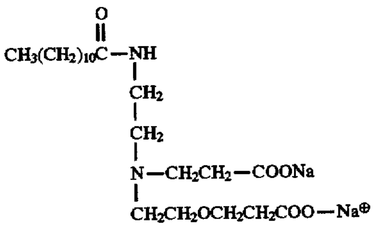

(II)

Compound (I) is capryloamphodipropionate and is commercially available from Lonza Corp. as Amphoterge® KJ-2. (In Lonza Amphoterge® KJ-2, the chain length of the lipophilic end, including the amide carbon, is $C_6$, 4%; $C_8$, 57%; $C_{10}$, 38% and $C_{12}$, 1%.) Compound II is cocoamphodipropionate and is commercially available from Lonza Corp. as Amphoterge® K-2 and from Witco Corporation as Rewoteric® AM2CSF.

The amphoteric surfactants may desirably be utilized in their salt-free forms, to maximize their compatibility in the glass cleaning systems, particularly if the glass cleaner contains detergents.

The quaternary compound of the present invention may be any compound which enhances the antifog activity of the amphoteric surfactant. For the purposes of this invention, such compounds include any conventional quaternary ammonium salt compounds in which a positively charged central nitrogen atom is joined to four organic groups associated with a negatively charged acid radical. The quaternary compounds are also intended to include other positively charged tetravalent nitrogen atom salts, including betaines and sulfobetaines.

Without being limited to this explanation, the inventor believes that the presence of the quaternary compound enhances the association of the amide tail of the amphoteric surfactant (which may be cationic) in conjunction with the amphoteric cationic group to the glass surface, leaving the anionic portion of the amphoteric compound free to promote antifog activity by lowering the surface tension at the glass surface.

Preferable quaternary compounds for use in the present invention are generally large and may be characterized as

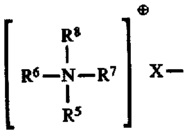

wherein $R^5$ is a straight chain or branched, saturated or unsaturated $C_{8-18}$ alkyl; $R^6$ and $R^7$ are independently 2-hydroxyethyl or (poly)ethoxyethanol; $R^8$ is a straight chain or branched, saturated or unsaturated $C_{1-8}$ organic moiety; and X is halogen, methyl sulfate or ethyl sulfate. Preferably, $R^5$ is a $C_{8-18}$ fatty acid, $R^6$ and $R^7$ are —$(CH_2—CH_2—O)_nCH_2CH_2$—OH wherein n=1–50 polyalkoxy groups (more preferably 10–25 polyalkoxy groups), $R^8$ is methyl or ethyl and X is chloride.

Suitable quaternary compounds include Witco Variquat® 66, known generically as ethyl bis (polyethoxy ethanol) tallow ammonium chloride and Nobel Berol® 563, known generally as alkyl polyglycol ether ammonium methyl sulfate. Variquat 66 has the formula

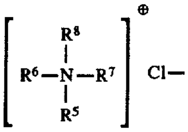

wherein $R^5$ is methyl, $R^6$ is tallow and $R^7$ and $R^8$ are both polyethoxy. Other suitable quaternary compounds include Witco Variquat® 638 and Variquat® K-1215; Rhone-Poulenc Rhodameen® VP-532/SPB and Miramine® OC.

Typically, glass cleaning compositions prepared in conformity with this invention will contain 0.05–2.0 weight percent amphoteric surfactant and 0.01–2.0 weight percent quaternary compound. Preferably, the compositions will contain 0.25–1.25 weight percent amphoteric surfactant and 0.075–1.25 weight percent quaternary compound and most preferably, 0.5–1.0 weight percent amphoteric surfactant and 0.1–1.0 weight percent quaternary compound.

Other chemicals may be added as desired. For instance, organic solvents may be used to speed drying time, reduce foaming and improve cleaning. The organic solvent may include alcohol. As used herein, "alcohol" is used collectively to refer to diols and glycols as well. Preferably the alcohols are $C_{1-9}$ and more preferably, $C_{3-6}$. Particularly preferred alcohols include propanol, isopropanol and hexanol.

Typically, in the compositions of the present invention, alcohol is present in the amount of 0–5.0 weight percent, preferably 0–4.0 weight percent and more preferably 1.0–3.0 weight percent.

Other compounds that are preferably utilized include amines, which may help raise the pH to the preferred range, causing the capryloamphodipropionate to become more anionic and hydrophilic. Suitable amines include, for instance, monoethanolamine, which also helps to improve cleaning and reduce interfacial tension.

Typically, in the compositions of the present invention, monoethanolamine is present in the amount of 0–1.5 weight percent, preferably 0–1.0 weight percent, more preferably 0.2–0.6 weight percent.

The preferred pH of the compositions of the present invention is basic, in order to cause the amphoteric surfactant to become more anionic and, as discussed above, more hydrophilic. Of course, the particular pH selected depends greatly upon the individual amphoteric surfactant which is utilized. Generally, however, the pH of the composition is above 7, more preferably from 8–13 and ideally from 10–11.

EXAMPLES

The following compositions are either illustrative Examples of various representative embodiments of the present invention, or Comparative Examples thereof.

Example I

An antifog glass-cleaning composition according to the present invention was prepared according to the following formula:

| | |
|---|---|
| capryloamphodipropionate | 0.7500 wt. % |
| ethyl bis (polyethoxy ethanol) tallow ammonium chloride | 0.2500 |
| monoethanolamine | 0.4000 |
| fragrance | 0.0400 |
| isopropyl alcohol | 2.0000 |

-continued

| | |
|---|---|
| direct blue 86 | 0.0004 |
| water | balance |

Example II

An antifog glass-cleaning composition according to the present invention was prepared according to the following formula:

| | |
|---|---|
| capryloamphodipropionate | 0.375 wt. % |
| cocoamphodipropionate | 0.375 |
| ethyl bis (polyethoxy ethanol) tallow ammonium chloride | 0.2500 |
| monoethanolamine | 0.4000 |
| fragrance | 0.0400 |
| isopropyl alcohol | 2.0000 |
| direct blue 86 | 0.0004 |
| water | balance |

Comparative Example I

A composition was prepared according to the following formula:

| | |
|---|---|
| capryloamphodipropionate | 0.7500 wt. % |
| ethyl bis (polyethoxy ethanol) tallow ammonium chloride | 0.7500 |
| monoethanolamine | 0.4000 |
| fragrance | 0.0400 |
| isopropyl alcohol | 2.0000 |
| direct blue 86 | 0.0004 |
| water | balance |

Comparative Example II

A composition was prepared in conformity with Example I except that 0.7500 wt. % Lonza Corp. Amphoterge® K was substituted for the capryloamphodipropionate. Amphoterge® K is cocoamphopropionate and has the formula:

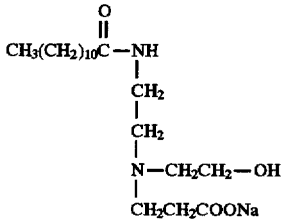

EVALUATION

As utilized by those skilled in the art, surface wetting and low contact angles are both understood to be good indicators of antifog activity. However, the present inventor has determined that high surface tension readings do not appear to have any correlation to antifog activity. Rather, causing the treated glass surface to become very hydrophilic appears to be a prerequisite to good antifog properties. Surface wetting and contact angles are good indicia of hydrophilicity.

Glass surfaces were treated by cleaning with the above compositions and then evaluated qualitatively by exposure to steam six to twelve inches from boiling water under ambient conditions of 72° F. and 40–60% relative humidity (RH). The compositions according to the present invention were found to provide highly fog-resistant treated surfaces that remained clear after five to seven days continuous exposure to steam, in contrast to those of the Comparative Examples, which fog immediately.

The treated glass surfaces were also evaluated quantitatively by a water drop test in which a 0.04 gram drop of tap water was placed on a mirror and the extent of spreading was measured after two minutes. It was found that water applied to glass treated with compositions according to Example I spread 17–18 mm, in contrast to drops deposited on an untreated mirror, which spread only 8–10 mm. It was also found that water applied to glass treated with compositions according to Example II spread 19–20 mm.

The compositions according to Example I and Comparative Example I were also evaluated for potentiation of antifog activity by measuring the contact angle of the compositions on mirrors. The composition of Example I provided a contact angle of 13.7, whereas the composition of Comparative Example I presented a contact angle of 31.7. As discussed above, causing the glass surface to become hydrophilic appears to be prerequisite to antifog activity. The composition according to Example I is streakless, low foaming during rub out, cleans and provides very good antifog activity.

Also, it was seen that the composition of Comparative Example II produces only about one-half the antifog activity of the composition of Example I. This difference is due primarily to the fact that the anionic moiety of cocoamphopropionate lacks the ether linkage of the anionic moiety of capryloamphodipropionate.

Although the present invention has been illustrated with reference to certain preferred embodiments, it will be appreciated that the present invention is not limited to the specifics set forth therein. Those skilled in the art readily will appreciate numerous variations and modifications within the spirit and scope of the present invention, and all such variations and modifications are intended to be covered by the present invention, which is defined by the following claims.

I claim:

1. An antifog composition for cleaning glass comprising:

water;

from about 0.05 to about 20% by weight of an amphoteric surfactant having the formula

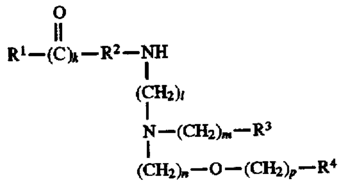

wherein:

$R^1$ is $C_{8-12}$ alkyl, $R^2$ is a single bond, k is 1, l is 1–3, m is 1 or 2, $R^3$ is —COOM (wherein M is H or alkali metal), n is 1–3, p is 1–3 and $R^4$ is —COOM; and from about 0.01 to about 2.0% by weight of a quaternary compound selected from the group consisting of positively charged tetravalent nitrogen atom salts, wherein said quaternary compound has the formula

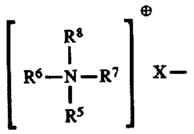

wherein $R^5$ is $C_{1-18}$ alkyl or fatty acid, $R^6$ and $R^7$ are independently 2-hydroxyethyl or (poly)ethoxyethanol, $R^8$ is a straight chain or branched, saturated or unsaturated $C_{1-8}$ organic moiety, and X is a halogen, methyl sulfate or ethyl sulfate.

2. The antifog glass cleaning composition according to claim 1, wherein $R^5$ is a $C_{8-18}$ fatty acid, and $R^6$ and $R^7$ are independently $—(CH_2—CH_2—O)_nCH_2CH_2—OH$ wherein n=1–50.

3. The antifog glass cleaning composition according to claim 3, wherein $R^7$ is methyl or ethyl, and X is chloride.

4. The antifog glass cleaning composition according to claim 2, wherein said amphoteric surfactant is present in the amount of 0.25–1.25 weight percent and said quaternary compound is present in the amount of 0.075–1.25 weight percent.

5. The antifog glass cleaning composition according to claim 3, wherein said amphoteric surfactant is present in the amount of 0.5–1.0 weight percent and said quaternary compound is present in the amount of 0.1–1.0 weight percent.

6. The antifog glass cleaning composition according to claim 1, further comprising from 0–5.0 weight percent alcohol and from 0–1.5 weight percent monoethanolamine.

7. The antifog glass cleaning composition according to claim 4, further comprising from 0–4.0 weight percent alcohol and from 0–1.0 weight percent monoethanolamine.

8. The antifog glass cleaning composition according to claim 5, further comprising from 1.0–3.0 weight percent alcohol and from 0.2–0.6 weight percent monoethanolamine.

9. The antifog glass cleaning composition according to claim 1, wherein k is 1, $R^3$ is —COOM, n is 1 or 2, and p is 1 or 2.

10. The antilog glass cleaning composition according to claim 9, wherein $R^1$ is $C_9$ alkyl, l is 2, m is 2, n is 2, and p is 1.

11. A method for creating a fog resistant surface comprising the steps of:

(a) treating a glass surface by applying an effective amount of a composition to said glass surface, the composition comprising:

water;

from about 0.05 to about 20% by weight of an amphoteric surfactant having the formula

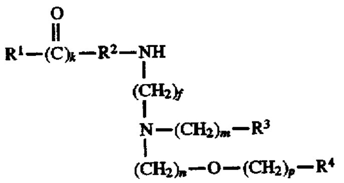

wherein:

$R^1$ is $C_{8-12}$ alkyl, $R^2$ is a single bond, k is 1, l is 1–3, m is 1 or 2, $R^3$ is —COOM (wherein M is H or alkali metal), n is 1–3, p is 1–3 and $R^4$ is —COOM; and from about 0.01 to about 2.0% by weight of quaternary compound selected from the group consisting of positively charged tetravalent nitrogen atom salts, wherein said quaternary compound has the formula

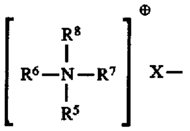

wherein $R^5$ is $C_{8-18}$ alkyl or fatty acid, $R^6$ and $R^7$ are independently 2-hydroxyethyl or (poly)ethoxyethanol, $R^8$ is a straight chain or branched, saturated or unsaturated $C_{1-8}$ organic moiety, and X is a halogen, methyl sulfate or ethyl sulfate; and (b) removing substantially all the residual composition from the glass surface.

12. The method of providing a fog resistant glass surface according to claim 11, wherein $R^5$ is a $C_{8-18}$ fatty acid and $R^6$ and $R^7$ are independently $—(CH_2—CH_2—O)_nCH_2CH_2—OH$ wherein n=1–50.

13. The method of providing a fog resistant surface according to claim 12, wherein $R^7$ is methyl or ethyl, and X is chloride.

14. The method of providing a fog resistant surface according to claim 12, wherein said amphoteric surfactant is present in the amount of 0.25–1.25 weight percent and said quaternary compound is present in the amount of 0.075–1.25 weight percent.

15. The method of providing a fog resistant surface according to claim 13, wherein said amphoteric surfactant is present in the amount of 0.5–1.0 weight percent and said quaternary compound is present in the amount of 0.1–1.0 weight percent.

16. The method of providing a fog resistant surface according to claim 14, wherein the antifog composition further comprises from 0–5.0 weight percent alcohol and from 0–1.5 weight percent monoethanolamine.

17. The method of providing a fog resistant surface according to claim 15, wherein the antifog composition further comprises from 0–4.0 weight percent alcohol and from 0–1.0 weight percent monoethanolamine.

18.The method of providing a fog resistant surface according to claim 16, wherein the antifog composition further comprises from 1.0–3.0 weight percent alcohol and from 0.2–0.6 weight percent monoethanolamine.

19. The method of providing a fog resistant glass surface according to claim 11, wherein k is 1, $R^3$ is —COOM, n is 1or 2, and p is 1 or 2.

20. The method of providing a fog resistant surface according to claim 19, wherein $R_1$ is $C_9$ alkyl, l is 2, m is 2, n is 2, and p is 1.

* * * * *